US00PP36584P2

(12) United States Plant Patent
Bunnik

(10) Patent No.: US PP36,584 P2
(45) Date of Patent: Apr. 1, 2025

(54) ***GUZMANIA* PLANT NAMED 'BUNGUZCE01'**

(50) Latin Name: ***Guzmania* sp. Ruiz & Pav.**
Varietal Denomination: BUNGUZCE01

(71) Applicant: 3B Fundus B.V., Kudelstaart (NL)

(72) Inventor: Bjorn Bunnik, Kudelstaart (NL)

(73) Assignee: 3B Fundus B.V., Kudelstaart (NL)

( * ) Notice: Subject to any disclaimer, the term of this patent is extended or adjusted under 35 U.S.C. 154(b) by 0 days.

(21) Appl. No.: 18/831,322

(22) Filed: Nov. 13, 2024

(51) Int. Cl.
*A01H 5/02* (2018.01)
*A01H 6/00* (2018.01)
*A01H 6/22* (2018.01)

(52) U.S. Cl.
USPC ..... Plt./371
CPC ..... *A01H 6/225* (2018.05)

(58) Field of Classification Search
USPC ..... Plt./371
See application file for complete search history.

*Primary Examiner* — Susan McCormick Ewoldt
(74) *Attorney, Agent, or Firm* — Samuel R. McCoy, Jr.

(57) ABSTRACT

A new and distinct variety of *Guzmania* plant named 'BUNGUZCE01' which is characterized by the combination of an upright growth habit, a tall plant height, long dark green foliage, a compound terminal inflorescence held above the foliage with large light pink bracts which subtend small lateral spikes of individual flowers, small white flowers that are subtended by a smaller pink floral bract which is tipped white, and the stability of all characteristics from generation to generation.

3 Drawing Sheets

Latin name of the genus and species: The Latin name of the genus and species of the novel variety disclosed herein is *Guzmania* sp. Ruiz & Pav.

Variety denomination: The inventive variety of *Guzmania* disclosed herein has been given the variety denomination 'BUNGUZCE01'.

BACKGROUND OF THE INVENTION

Parentage: The *Guzmania* variety 'BUNGUZCE01' is the result of a naturally occurring, whole-plant mutation of *Guzmania* hybrid 'Viola' (U.S. Plant Pat. No. 13,679), discovered at a commercial plant nursery in Kudelstaart, the Netherlands. In June of 2014, the inventor observed one plant growing amongst a cultivated crop of 'Viola' plants that exhibited lighter pink inflorescence, relative to all other plants of the population. The mutated plant was isolated for further evaluation. Upon confirmation of distinctness and stability, the new *Guzmania* plant was given the name 'BUNGUZCE01'.

Asexual Reproduction: 'BUNGUZCE01' was first asexually propagated by way of meristematic tissue culture micropropagation in the summer of 2014 at a commercial tissue culture laboratory in Aalsmeer, the Netherlands. Through 15 subsequent generations, the unique features of this cultivar are stable and reproduced true to type.

SUMMARY OF THE INVENTION

The cultivar 'BUNGUZCE01' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'BUNGUZCE01'. These characteristics, in combination, distinguish 'BUNGUZCE01' as a new and distinct *Guzmania* cultivar:

1. *Guzmania* 'BUNGUZCE01' exhibits an upright monopodial growth habit with a relatively tall plant height; and
2. *Guzmania* 'BUNGUZCE01' exhibits long, dark green foliage; and
3. *Guzmania* 'BUNGUZCE01' exhibits a compound terminal spike inflorescence, held above the foliage, and bearing smaller lateral spikes of individual flower, each subtended by a large, showy light red-purple bract; and
4. *Guzmania* 'BUNGUZCE01' exhibits small white flowers that are enveloped by red-purple floral bracts which are tipped white.

BOTANICAL DESCRIPTION OF THE PLANT

Figure 1:
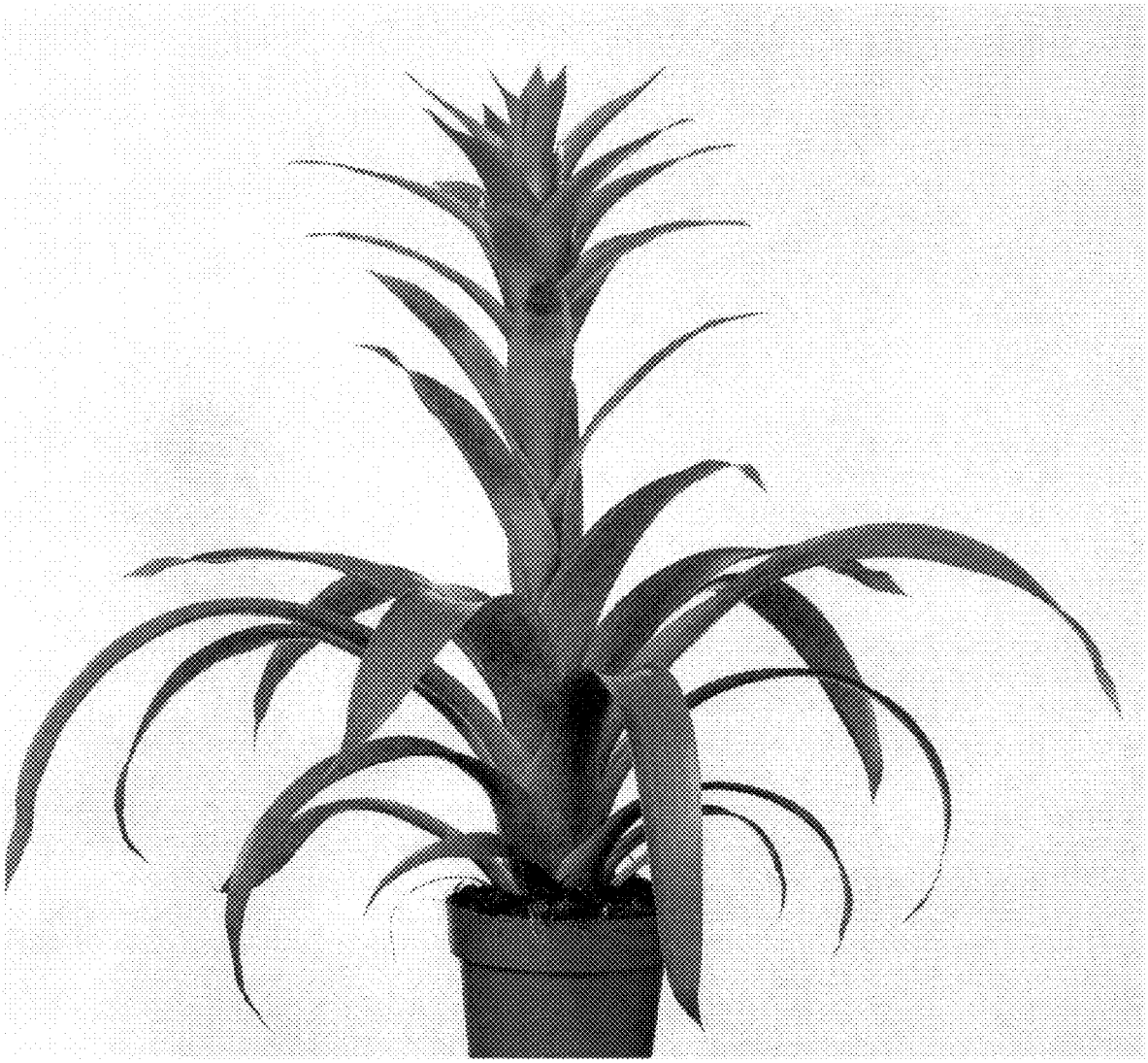
FIG. 1 illustrates, as nearly true as it is reasonably possible to make the same in color photographs of this type, an exemplary plant of 'BUNGUZCE01' grown in a commercial greenhouse in Kudelstaart, the Netherlands. This plant is approximately 18 months old, shown planted in a 12 cm container.
Figure 2:
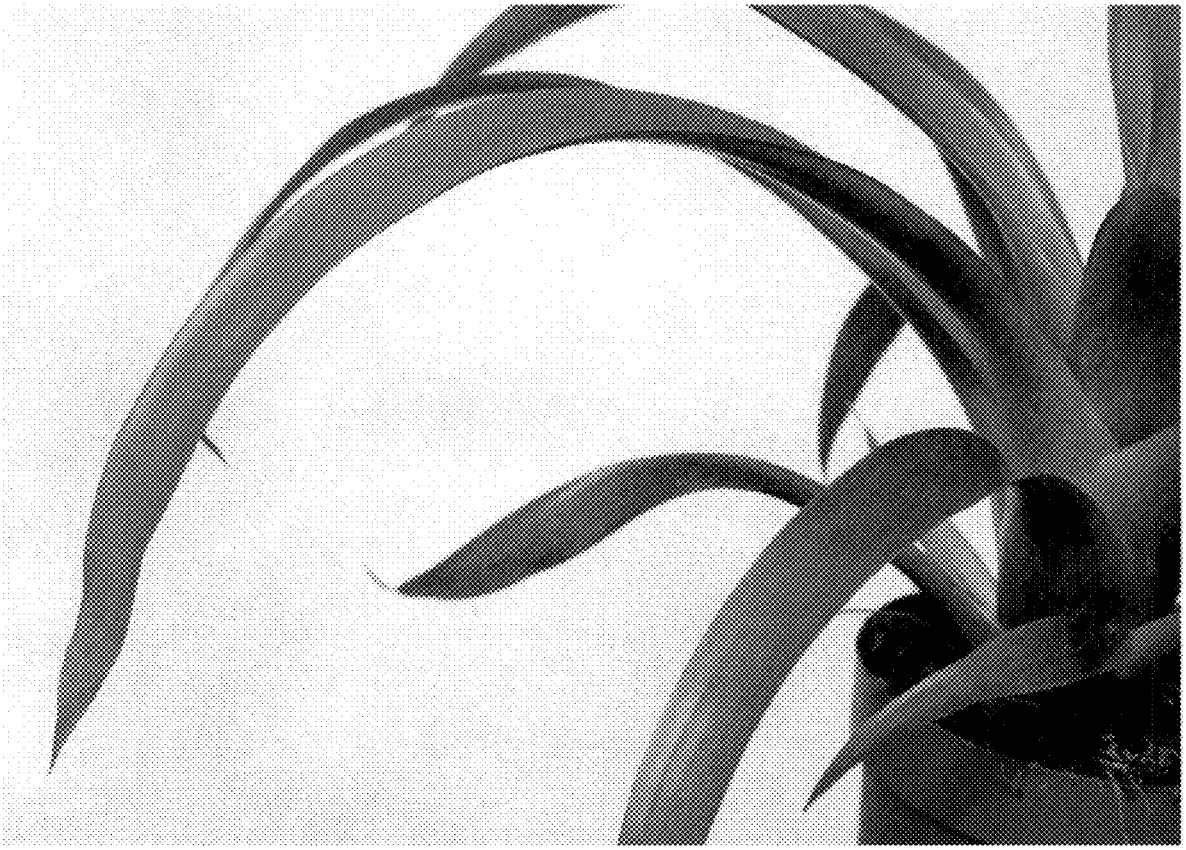
FIG. 2 illustrates, as nearly true as it is reasonably possible to make the same in color photographs of this type, the mature foliage of 'BUNGUZCE01'.
Figure 3:
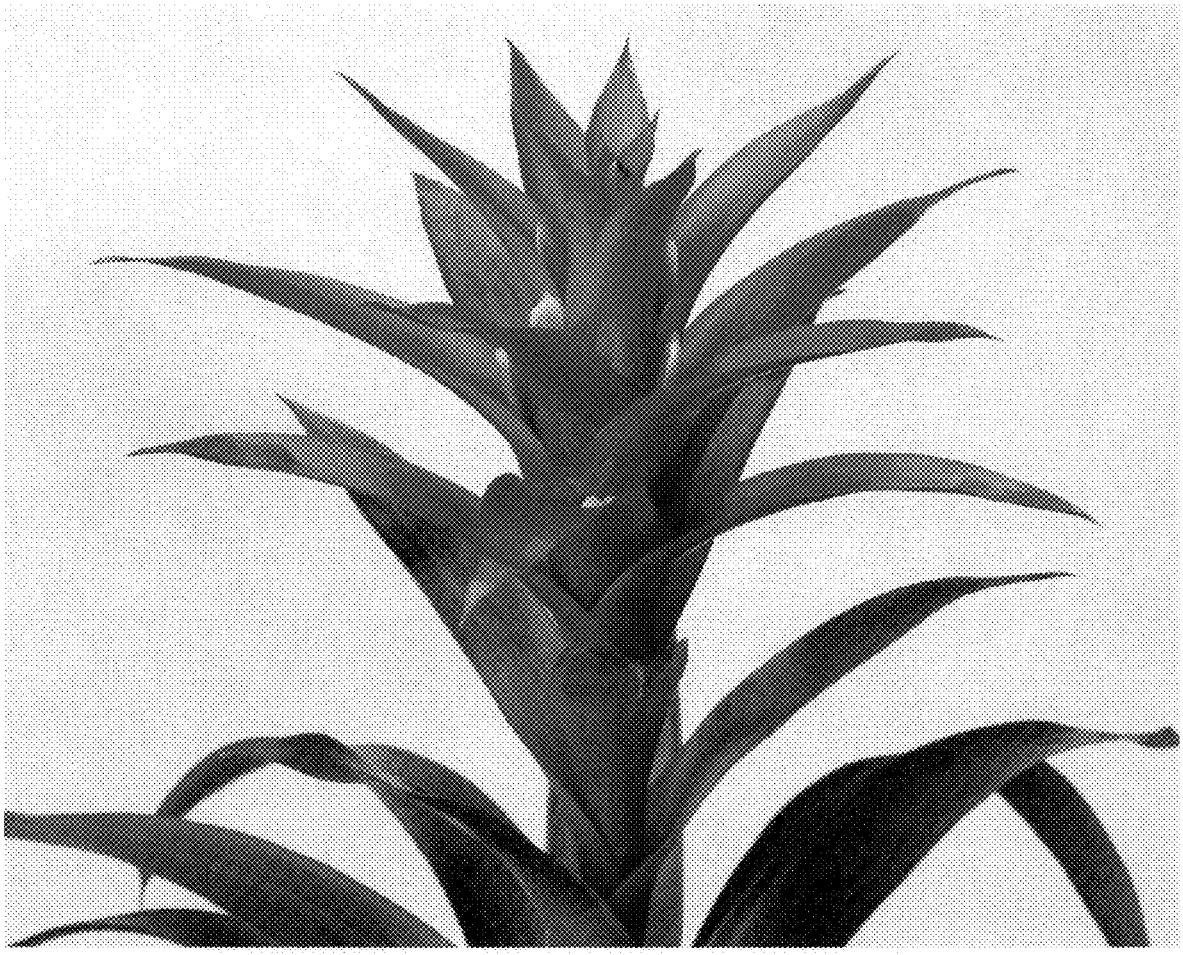
FIG. 3 illustrates, as nearly true as it is reasonably possible to make the same in color photographs of this type, the inflorescence of 'BUNGUZCE01'.

The following observations and measurements, made in November of 2023, describe averages from a sample set of six specimens of 18 month-old 'BUNGUZCE01' plants grown in 12 cm nursery pots at a commercial greenhouse in Kudelstaart, the Netherlands. Plants were grown under approximately 50-percent shade cloth and maintained with a 1.0 EC fertigation program with regular overhead irrigation. No chemical pest measures were taken.

Those skilled in the art will appreciate that certain characteristics will vary with older or, conversely, with younger plants. 'BUNGUZCE01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, Sixth Edition.

A botanical description of 'BUNGUZCE01' and a comparison with the parent plant and most similar variety of *Guzmania* are provided below.

Plant description:

*Growth habit*.—Perennial; monopodial; broad, upright. Leaves arranged in a funnel shaped basal rosette, with no lateral branching, and the inflorescence growing from the center of the basal rosette and held above the foliage.

*Plant form*.—Flattened globular.

*Average height*.—29.0 cm, from the soil level to the top of the foliar plane, and 40.3 cm to the top of the floral plane.

*Plant spread*.—Average of 50.5 cm.

*Growth rate*.—Moderately fast.

*Plant vigor*.—Moderately vigorous.

*Propagation type*.—Vegetative cuttings and meristematic tissue culture.

*Time to initiate roots*.—Approximately 22 days at 21 degrees Celsius.

*Time to produce a marketable plant*.—Approximately 70 weeks at 21 degrees Celsius in a 12.0 cm nursery container.

*Pest resistance and susceptibility*.—Typical resistance and susceptibility to other *Guzmania* varieties.

*Temperature tolerances*.—USDA Zones 10 to 13; at least tolerant of temperatures to 40 degrees Celsius. High tolerance to wind and rain inundations.

Root system:

*General*.—Thick; medium density.

*Texture*.—Slightly fleshy.

Foliage:

*Arrangement*.—Basal rosulate. No stems or lateral branches.

*Attachment*.—Sessile.

*Division*.—Simple.

*Quantity of leaves*.—18.

*Lamina*.—Dimensions — 41.2 cm long and 4.0 cm wide. Shape of blade — Ensiform. Aspect — Moderately concave and curled downward. Attitude — Upright and moderately reflexed. Apex — Apiculate. Base — Sheathing. Margin — Entire, unlobed; not undulated. Pubescence, texture and luster of adaxial surface — Glabrous, non-rugose and slightly glossy. Pubescence, texture and luster of abaxial surface — Glabrous, non-rugose and slightly glossy. Color — Juvenile foliage, adaxial surface — Green, nearest to RHS 143A. Juvenile foliage, abaxial surface — Yellow-green, nearest to RHS 146B. Mature foliage, adaxial surface — Green, slightly darker than a blend of RHS 137B and 143A yet nearest to 137B. Mature foliage, abaxial surface — Yellow-green, nearest to RHS 146B. Venation — Pattern — Parallel. Mature foliage venation, adaxial surface — Green, slightly darker than a combination of RHS 137B and 143A yet nearest to 137B. Mature foliage venation, abaxial surface — Yellow-green, nearest to RHS 146B. Sheath — Sheath dimensions — 9.3 cm long and 7.2 cm wide. Sheath Color — Greyed-yellow; near 160A and 160B.

Inflorescence:

*Inflorescence arrangement*.—Terminal compound spike bearing an average of 12 smaller spikes, each subtended by a large, showy bract; the small spikes bear an average of 9 individual flowers which are themselves subtended by a floral bract.

*Natural flowering season*.—Continuous flowering.

*Time to flower*.—Approximately 6 months.

*Inflorescence quantity*.—One.

*Flowers per inflorescence*.—Average of 108.

*Inflorescence height*.—Approximately 15.4 cm (measured from base of lowest flower to top of upper flower).

*Inflorescence diameter*.—Average of 4.6 cm, excluding bracts, and 21.6 cm with bracts.

*Large bracts subtending each flower cluster spike*.—Quantity — Average of 12. Shape — Lanceolate. Dimensions — Average of 11.4 cm long and 3.0 cm wide. Apex — Acuminate. Base — Sheathing. Margins — Entire. Texture and luster — Smooth, glabrous, and moderately glossy. Color, upper surface — Red-purple, RHS 67B; lower bracts are tipped green, RHS 143, at and near the apex. Color, lower surface — Red-purple, nearest to a blend of RHS 67B and 67C; lower bracts are tipped yellow-green, nearest to RHS 146B, at and near the apex. Sheath — Sheath length — Average 3.5 cm. Sheath width — Average 4.9 cm. Sheath color, upper surface — Nearest to a blend of yellow-green and greyed-yellow, RHS 153D and 160A. Sheath color, lower surface — Yellow-green, nearest to RHS 152B, and transitioning to greyed-orange at the base, RHS N167A.

*Peduncle*.—Dimensions — Approximately 26.0 cm long and 0.9 cm in diameter. Attitude — Vertical, angle at which peduncle sits compared to the lateral branch axis is 0-degrees. Strength — Strong. Texture and luster — Glabrous, smooth, and glossy. Color — Yellow-green to greyed-yellow, nearest to a combination of RHS 150D and 160D.

Bud:

*Length*.—Average of 1.9 cm.

*Diameter*.—Average of 0.25 cm.

*Shape*.—Lanceolate.

*Texture and luster*.—Glabrous, smooth, and moderately glossy.

*Color*.—Green-white, nearest RHS 157A; the upper portion, approximately two-thirds of the way, is translucent white, nearest to RHS NN155D.

Flower:

*Flower type and form*.—Lanceolate.

*Attachment*.—Sessile.

*Attitude*.—Upright.

*Height*.—Approximately 0.5 cm.

*Width*.—Average of 0.5 cm.

*Depth*.—Approximately 3.5 cm.

*Fragrance*.—No fragrance.

*Lastingness*.—4 weeks.

*Persistence*.—Persistent self-cleaning.

*Texture and luster*.—Both sides of the flower are smooth and glabrous.

*Petals*.—Quantity of Petals — 3. Arrangement — Rotate; single whorl; petals free. Length — Approximately 1.5 cm. Width — Approximately 0.4 cm. Shape — Oblong. Aspect — Concave. Apex — Obtuse. Base — Cuneate. Margin — Entire; not undulated. Pubescence, texture and luster of upper surface — Glabrous, smooth and slightly glossy. Pubescence, texture and luster of lower surface — Glabrous, smooth and slightly glossy. Color when opening, upper surface — White, nearest to RHS NN155C. Color when opening, lower surface — White, nearest to RHS NN155C. Color when fully opened, upper surface — White, nearest to RHS NN155C. Color when fully opened, lower surface — White, nearest to RHS NN155C. Fading, upper surface — Not fading. Fading, lower surface — Not fading. Venation color, fully opened, upper surface — No venation is visible. Venation color, fully opened, lower surface — No venation is visible.

*Calyx*.—Shape — Rotate. Length — Average of 3.2 cm. Diameter — Average of 0.5 cm.

*Sepals*.—Quantity — 3 unfused sepals in a single whorl. Arrangement — Rotate. Length — 3.2 cm. Width — 0.45 cm. Shape — Lanceolate. Aspect — Strongly concave. Apex — Narrow acuminate. Base — Cuneate. Margin — Entire. Pubescence, texture and luster of upper surface — Glabrous, smooth, and moderately glossy. Pubescence, texture and luster of lower surface — Glabrous, smooth, and moderately glossy. Color when opening, upper surface — Translucent white, nearest to RHS NN155A. Color when opening, lower surface — Translucent white, nearest to RHS NN155A. Color when fully opened, upper surface — Translucent white, nearest to RHS NN155A. Color when fully opened, lower surface — Translucent white, nearest to RHS NN155A.

*Floral bracts*.—Shape — Oblong yet folded to envelop the flower. Aspect — Concave. Dimensions, when unfolded — Average of 5.6 cm long, including the sheath, and 2.1 cm wide. Apex — Bluntly acute. Base — Broad cuneate. Margins — Entire. Texture and luster, upper surface — Smooth and moderately glossy. Texture and luster, lower surface — Smooth and moderately glossy. Color, upper surface — The base of the bract is translucent white, nearest to RHS 155B; bracts becoming increasingly suffused and ultimately transitioning entirely to red-purple, nearest to RHS N74D, for approximately the distal two-thirds portion of the bract; bracts tipped with white, nearest to NN155B. Color, lower surface — The base of the bract is translucent white, nearest to RHS 155A; bracts becoming increasingly suffused and ultimately transitioning entirely to red-purple, nearest to RHS N74D, for approximately the distal two-thirds portion of the bract; bracts tipped with white, nearest to NN155B.

Reproductive organs:

*Stamens*.—Quantity — 6, on average. Anthers — Attachment — Dorsifixed. Shape — Narrow sagittate. Dimensions — Average of 0.7 cm long and 0.1 cm wide. Color — White, nearest to RHS 155A. Filaments — Length — 0.9 cm, on average. Color — White, nearest to RHS 155D. Pollen — None detected.

*Pistil*.—Quantity — 1. Length — 0.8 cm. Style — Length — 0.65 cm. Color — White, nearest to RHS 155C. Stigma — Shape — Cleft, fringed, three-parted. Dimensions — Average of 0.15 cm long and 0.15 cm wide. Color — White, nearest to RHS 155D. Ovary Color — Green-white, nearest to RHS 157C.

Fruit and seed: To date, not observed.

COMPARISONS WITH THE PARENT PLANT

Plants of the new cultivar 'BUNGUZCE01' differ from its parent, *Guzmania* hybrid 'Viola' (U.S. Plant Pat. No. 13,679), by the characteristics described in Table 1.

TABLE 1

| Characteristic | 'BUNGUZCE01' | 'Voila' |
|---|---|---|
| General coloration of the foliage. | A darker shade of green relative to 'Viola'. The foliage is homogenously green. | A lighter shade of green relative to 'BUNGUZCE01', with splotches of light brown suffusion. |
| General coloration of the large showy bracts. | A lighter shade of red-purple relative to 'Viola'. | A darker shade of red-purple relative to 'BUNGUZCE01'. |

COMPARISON WITH THE MOST SIMILAR *GUZMANIA* CULTIVAR KNOWN TO THE INVENTOR

'BUNGUZCE01' is similar in many horticultural characteristics to the commercial cultivar *Guzmania* sp. 'G9197' (U.S. Plant Pat. No. 28,212). However, 'BUNGUZCE01' differs from 'G9197' by the characteristics described in Table 2.

TABLE 2

| Characteristic | 'BUNGUZCE01' | 'G9197' |
|---|---|---|
| Plant size. | Taller than 'G9197'. | Shorter than 'BUNGUZCE01'. |
| Foliage length. | Longer than 'G9197'. | Shorter than 'BUNGUZCE01'. |
| General coloration of the large showy bracts. | A lighter shade of red-purple relative to 'G9197'. | A darker shade of red-purple relative to 'BUNGUZCE01'. |
| Flower size. | Larger than 'G9197'. | Smaller than 'BUNGUZCE01'. |
| Quantity of flowers per inflorescence. | Less flowers than 'G9197'. | More flowers than 'BUNGUZCE01'. |

That which is claimed is:

1. A new and distinct variety of *Guzmania* plant named 'BUNGUZCE01', substantially as described and illustrated herein.

* * * * *